United States Patent
Alessi et al.

(10) Patent No.: US 9,353,128 B2
(45) Date of Patent: May 31, 2016

(54) DISUBSTITUTED NAPHTHOHETERODIAZOLE COMPOUNDS

(71) Applicant: ENI S.p.A., Rome (IT)

(72) Inventors: Andrea Alessi, Novara (IT); Samuele Santarelli, Novara (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 14/250,687

(22) Filed: Apr. 11, 2014

(65) Prior Publication Data

US 2014/0309431 A1  Oct. 16, 2014

(51) Int. Cl.
*C07D 519/00* (2006.01)
*H01L 31/055* (2014.01)

(52) U.S. Cl.
CPC ............ *C07D 519/00* (2013.01); *H01L 31/055* (2013.01); *Y02E 10/52* (2013.01)

(58) Field of Classification Search
CPC ... C07D 495/04; C07D 519/00; H01L 31/055
See application file for complete search history.

(56) References Cited

U.S. PATENT DOCUMENTS

2013/0001474 A1    1/2013  Caldararo et al.

FOREIGN PATENT DOCUMENTS

| WO | WO 2011/072876 A1 |   | 6/2011 |
| WO | WO 2012007834 A1 | * | 1/2012 |
| WO | WO 2012/111811 A1 |   | 8/2012 |
| WO | WO 2013/005177 A2 |   | 1/2013 |
| WO | WO 2013098726 A1 | * | 7/2013 |

OTHER PUBLICATIONS

Italian Search Report issued Sep. 9, 2013 in IT Application MI2013 0606, filed on Apr. 12, 2013 ( with English Translation of Categories of Cited Documents).

Huaxing Zhou et al. "Donor-Acceptor Polymers Incorporating Alkylated Dithienylbenzothiadiazole for Bulk Heterojunction Solar Cells: Pronounced Effect for Positioning Alkyl Chains", Macromolecules Article, 2010, 10 pages.
U.S. Appl. No. 14/250,673, filed Apr. 11, 2014, Santarelli, et al.

* cited by examiner

*Primary Examiner* — Matthew Coughlin
(74) *Attorney, Agent, or Firm* — Oblon, McClelland, Maier & Neustadt, L.L.P.

(57) ABSTRACT

Disubstituted naphthoheterodiazole compound having general formula (I):

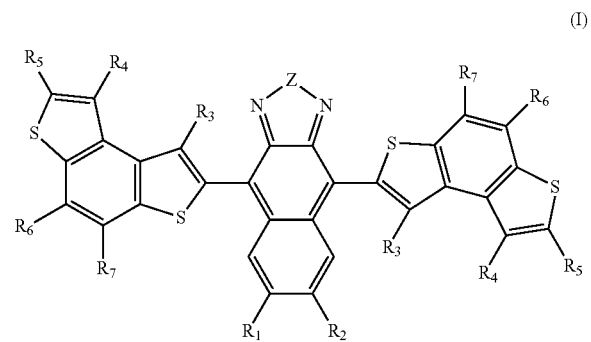

wherein:
Z represents a heteroatom selected from oxygen (O), sulfur (S), selenium (Se), tellurium (Te), preferably sulfur (S);
$R_1$, $R_2$, $R_3$, $R_4$, $R_5$, $R_6$ and $R_7$, equal to or different from each other, represent a hydrogen atom; or they are selected from n-butyl, iso-butyl, sec-butyl, t-butyl.
Said disubstituted naphthoheterodiazole compound having general formula (I) can be advantageously used as spectrum converter in luminescent solar concentrators (LSCs), in its turn capable of improving the performances of photovoltaic devices (or solar devices) selected, for example, from photovoltaic cells (or solar cells), photovoltaic modules (or solar modules), on both rigid and flexible supports.

10 Claims, 1 Drawing Sheet

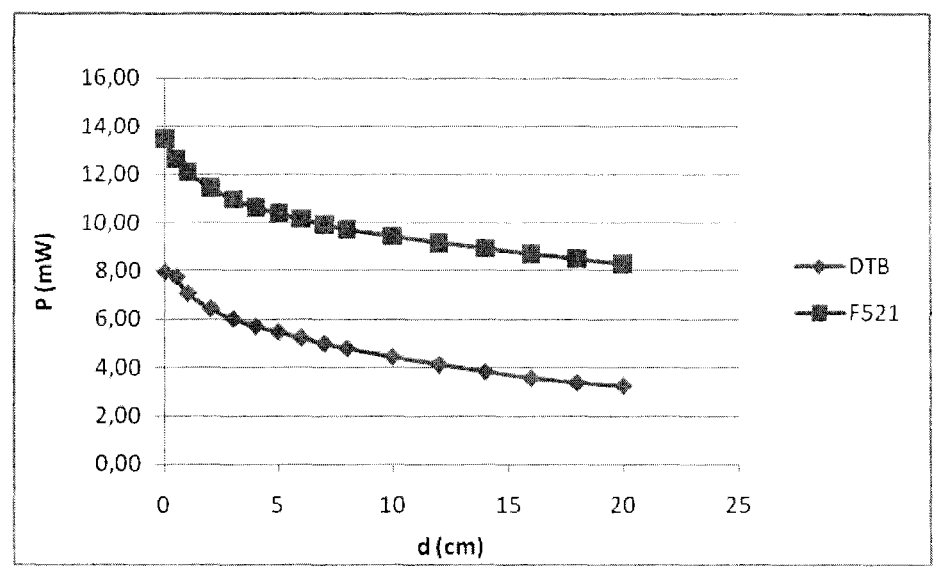

DISUBSTITUTED NAPHTHOHETERODIAZOLE COMPOUNDS

CROSS-REFERENCE TO RELATED APPLICATIONS

This application is based upon and claims the benefit of priority to Italian Application No. MI2013A 000606 filed on Apr. 12, 2013.

The present invention relates to a disubstituted naphthoheterodiazole compound.

More specifically, the present invention relates to a naphthoheterodiazole compound disubstituted with benzodithiophene groups.

The present invention also relates to a process for the preparation of said naphthoheterodiazole compound disubstituted with benzodithiophene groups.

Said naphthoheterodiazole compound disubstituted with benzodithiophene groups can be advantageously used as spectrum converter in luminescent solar concentrators (LSCs), in their turn capable of improving the performances of photovoltaic devices (or solar devices) selected, for example, from photovoltaic cells (or solar cells), photovoltaic modules (or solar modules), on both rigid and flexible supports.

The present invention also relates to a luminescent solar concentrator (LSC) including at least a naphthoheterodiazole compound disubstituted with benzodithiophene groups, and also to a photovoltaic device (or solar device) comprising said luminescent solar concentrator (LSC).

It is known that neither polymer nor silicon photovoltaic cells (or solar cells) which are currently the most widely-used on the market, are capable of efficiently exploiting all solar radiation. Their efficiency, in fact, is maximum only within a certain spectrum range which comprises a part of visible radiation and a part of infrared radiation.

Spectrum converter materials capable of capturing solar radiation outside the optimal spectral range and of converting it to effective radiation, can be used for enhancing the performance of photovoltaic cells (or solar cells). Luminescent solar concentrators (LSCs) can be produced with these materials, which allow a further increase in the production of current in photovoltaic cells (or solar cells).

Said luminescent solar concentrators (LSCs) generally consist of large sheets of material transparent to solar radiation, in which fluorescent substances are dispersed, or chemically bound to said material, which act as spectrum converters. Due to the effect of the optical phenomenon of total reflection, the radiation emitted by the fluorescent molecules is "guided" towards the thin edges of the sheet where it is concentrated on photovoltaic cells (or solar cells) positioned therein. In this way, large surfaces of low-cost materials (photoluminescent sheets) can be used for concentrating the light on small surfaces of high-cost materials [photovoltaic cells (or solar cells)].

A fluorescent compound should have numerous characteristics for being advantageously used in the construction of luminescent solar concentrators (LSCS) and these are not always compatible with each other.

First of all, the frequency of the radiation emitted by fluorescence must correspond to an energy higher than the threshold value below which the semiconductor, representing the core of the photovoltaic cell (or solar cell), is no longer able to function.

Secondly, the absorption spectrum of the fluorescent compound should be as extensive as possible, so as to absorb most of the inciding solar radiation and then re-emit it at the desired frequency.

It is also desirable that the absorption of the solar radiation be extremely intense, so that the fluorescent compound can exert its function at the lowest possible concentrations, avoiding the use of extremely large quantities of the same.

Furthermore, the absorption process of solar radiation and of its subsequent re-emission at lower frequencies, must take place with the highest possible efficiency, minimizing the so-called non-radiative losses, often collectively indicated with the term "thermalization": the efficiency of the process is measured by its quantic yield.

Finally, the absorption and the emission frequencies must be as diverse as possible, as otherwise the radiation emitted by a molecule of the fluorescent compound would be absorbed and at least partially diffused by the adjacent molecules. Said phenomenon, generally called self-absorption, inevitably leads to a significant loss in efficiency. The difference between the frequencies of the peak with the lower frequency of the absorption spectrum and the peak of the radiation emitted, is normally indicated as Stokes shift and measured as nm (i.e. it is not the difference between the two frequencies that is measured, but the difference between the two wavelengths which correspond to them). High Stokes shifts are absolutely necessary for obtaining high efficiencies of luminescent solar concentrators (LSCs), bearing in mind the necessity, already mentioned, that the frequency of the radiation emitted corresponds to an energy higher than the threshold value below which the photovoltaic cell (or solar cell) is not able to function.

It is known that some benzothiadiazole compounds, in particular 4,7-di(thien-2'-yl)-2,1,3-benzothiadiazole (DTB), are fluorescent compounds which can be used in the construction of luminescent solar concentrators (LSCs). Compounds of this type are described in international patent application WO 2011/048458 in the name of the Applicant.

4,7-di(thien-2'-yl)-2,1,3-benzothiadiazole (DTB) is characterized by an emission centred around 579 nm, which corresponds to an energy well above the minimum threshold value for the functioning of the photovoltaic cells (or solar cells), said threshold corresponding, for example, to a wavelength of about 1,100 nm for the most widely-used photovoltaic cells (or solar cells), based on silicon. Furthermore, its absorption of light radiation is intense and extends over a relatively wide range of wavelengths, indicatively ranging from 550 nm (green radiation wavelength) to ultraviolet. Finally, 4,7-di(thien-2'-yl)-2,1,3-benzothiadiazole (DTB) has a Stokes shift, in dichloromethane solution, equal to 134 nm, well above that of most of the commercial products so far proposed for use in luminescent solar concentrators (LSCs).

For these reasons, the use of 4,7-di(thien-2'-yl)-2,1,3-benzothiadiazole (DTB) has enabled the production of high-quality luminescent solar concentrators (LSCs).

Although 4,7-di(thien-2'-yl)-2,1,3-benzothiadiazole (DTB) absorbs a significant part of the solar spectrum, however, it has a modest absorption in its higher wavelength regions, corresponding to yellow and red radiations which cannot therefore be converted into other radiations more effectively exploited by the photovoltaic cell (or solar cell). For this reason, it is desirable to avail of fluorescent products having a wider absorption spectrum towards red, high Stokes shifts, and good absorption coefficients.

The Applicant has therefore considered the problem of finding photoluminescent compounds having the characteristics indicated above and, in particular, a wider absorption spectrum towards red, high Stokes shifts and good absorption coefficients.

The Applicant has now found that disubstituted naphthoheterodiazole compounds having a specific general formula (i.e. having general formula (I) indicated hereunder), have good characteristics in terms of frequency of the radiations emitted, of intensity and absorption efficiency, of re-emission, of adequate diversity between the absorption and emission frequencies. Said disubstituted naphthoheterodiazole compounds have a much wider absorption spectrum towards red with respect to the known benzothiadiazole compounds. Furthermore, said disubstituted naphthoheterodiazole compounds have higher Stokes shifts with respect to those of the known benzothiadiazole compounds. Said disubstituted naphthoheterodiazole compounds can be advantageously used in the construction of luminescent solar concentrators (LSCs). Said luminescent solar concentrators (LSCs) can be advantageously used in the construction of photovoltaic devices (or solar devices) such as, for example, photovoltaic cells (or solar cells), photovoltaic modules (or solar modules), both on rigid and flexible supports An object of the present invention therefore relates to a disubstituted naphthoheterodiazole compound having general formula (I):

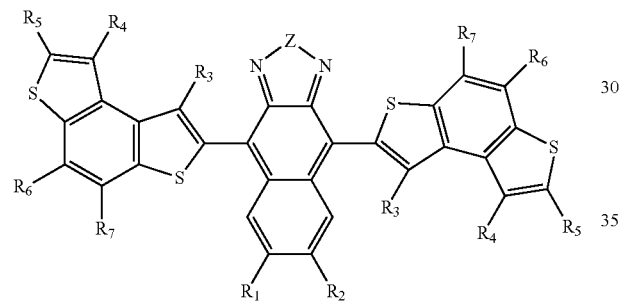

(I)

wherein:
Z represents a heteroatom selected from oxygen (O), sulfur (S), selenium (Se), tellurium (Te), preferably sulfur (S);
$R_1$, $R_2$, $R_3$, $R_4$, $R_5$, $R_6$ and $R_7$, equal to or different from each other, represent a hydrogen atom; or they are selected from n-butyl, iso-butyl, sec-butyl, t-butyl.

According to a preferred embodiment of the present invention, in said general formula (I), Z is sulfur, $R_1$, $R_2$, $R_3$, $R_4$ and $R_5$, are hydrogen and $R_6$ and $R_7$, are n-butyl.

A particularly preferred aspect of the present invention therefore relates to 4,9-bis(7',8'-dibutylbenzo[1',2'-b':4',3'-b"]dithien-5'-yl)-naphtho[2,3-c][1,2,5]thiadiazole having formula (Ia)

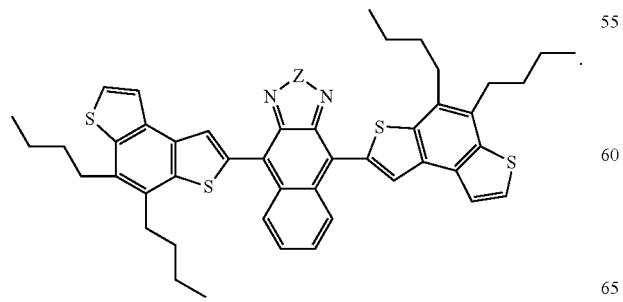

(Ia)

As mentioned above, the disubstituted naphthoheterodiazole compound having general formula (I), has an adsorption which, with respect to that of 4,7-di(thien-2'-yl)-2,1,3-benzothiadiazole (DTB) extends to a much greater extent towards red: said absorption is intense and extensive over a relatively wide wavelength range which, for example, for 4,9-bis(7',8'-dibutylbenzo[1',2'-b':4',3'-b"]dithien-5'-yl) naphtho[2,3-c][1,2,5]thiadiazole having formula (Ia) ranges from 230 to 650 nm. Furthermore, said disubstituted naphthoheterodiazole compound having general formula (I) has a particularly high Stokes shift. 4,9-bis(7',8'-dibutylbenzo[1', 2'-b':4',3'-b"]dithien-5'-yl)naphtho[2,3-c][1,2,5]thiadiazole having formula (Ia), for example, has a Stokes shift, in dichloromethane solution, equal to 246 nm: therefore, a Stokes shift higher than that, already high, of 4,7-di(thien-2'-yl)-2,1,3-benzothiadiazole (DTB) equal to 134 nm (measured under the same conditions).

For the aim of the present description and of the following claims, the definitions of the numerical ranges always comprise the extremes unless otherwise specified.

For the aim of the present description and of the following claims, the term "comprising" also includes the terms "which essentially consists of" or "which consists of".

The present invention also relates to a process for the preparation of the disubstituted naphthoheterodiazole compound having general formula (I).

A further object of the present invention therefore relates to a process for the preparation of a disubstituted naphthoheterodiazole compound having general formula (I) which comprises reacting at least one disubstituted naphthoheterodiazole compound having general formula (II):

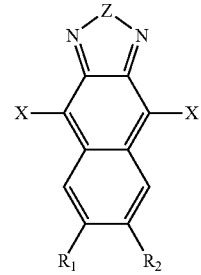

(II)

wherein X represents a halogen atom selected from chlorine, bromine, iodine, preferably bromine, Z, $R_1$ and $R_2$ have the same meanings described above;
with at least one monostannylated benzodithiophene compound having general formula (III):

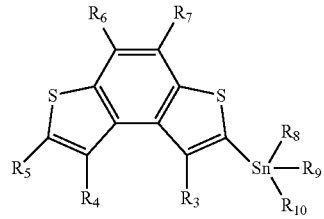

(III)

wherein $R_3$, $R_4$, $R_5$, $R_6$ and $R_7$, have the same meanings described above, and $R_8$, $R_9$ and $R_{10}$, equal to or different from each other, represent a hydrogen atom, or they are selected from linear or branched $C_1$-$C_{20}$, preferably $C_2$-$C_{10}$, alkyl groups, or cycloalkyl groups optionally substituted.

The above process can be carried out according to the following Scheme 1:

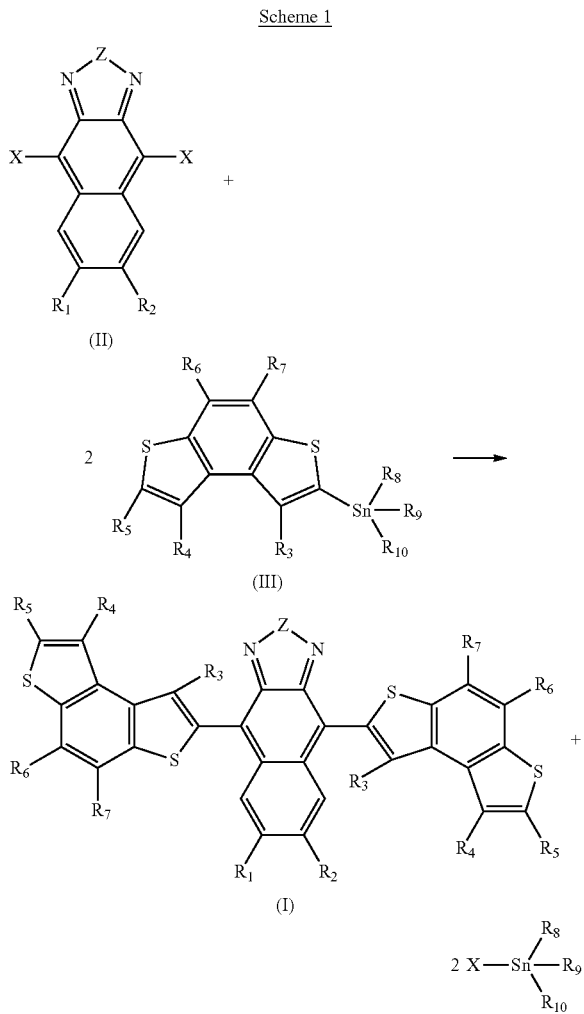

wherein Z, X, $R_1$, $R_2$, $R_3$, $R_4$, $R_5$, $R_6$, $R_7$, $R_8$, $R_9$ and $R_{10}$, have the same meanings described above.

According to a preferred embodiment of the present invention, said disubstituted naphthoheterodiazole compound having general formula (II) and said monostannylated benzodithiophene compound having general formula (III) can be used in molar ratios ranging from 1:2 to 1:4, preferably ranging from 1:2 to 1:2.1.

According to a further preferred embodiment of the present invention, said process relates to the preparation of 4,9-bis(7', 8'-dibutylbenzo[1',2'-b':4',3'-b'']dithien-5'-yl)-naphtho[2,3-c][1,2,5]thiadiazole having formula (Ia).

According to a further preferred embodiment of the present invention, said process can be carried out in the presence of at least one catalyst containing palladium.

According to a further preferred embodiment of the present invention, said catalyst containing palladium can be selected from: compounds of palladium in oxidation state (0) or (II), preferably in oxidation state II.

Specific examples of catalyst containing palladium which can be advantageously used for the aim of the present invention are:

dichloro[bis(triphenylphosphine)]palladium(II) [Pd(PPh$_3$)$_2$Cl$_2$];
[bis(triphenylphosphine)]palladium(II) diacetate [Pd(PPh$_3$)$_2$(AcO)$_2$];
tetrakis(triphenylphosphine)palladium(0) [Pd(PPh$_3$)$_4$];
bis(dibenzylideneacetone)palladium (0) [Pd(dba)$_2$ wherein dba=$C_6H_5$CH=CHCOCH=CHC$_6$H$_5$];
dichloro[bis(acetonitrile)]palladium(II) [Pd(CH$_3$CN)$_2$Cl$_2$];
benzylchloro[bis(triphenylphosphine)]palladium(II) [C$_6$H$_5$CH$_2$Pd(PPh$_3$)$_2$Cl];
or mixtures thereof.

Said catalyst containing palladium is preferably dichloro[bis(triphenylphosphine)]palladium(II) [Pd(PPh$_3$)$_2$Cl$_2$].

Said catalyst based on palladium can optionally be prepared in situ operating according to known techniques, by adding, to the reaction mixture, a palladium salt and a suitable ligand, dissolved in the reaction solvent selected from those indicated hereunder [for example, non-anhydrous dimethylsulfoxide (DMSO), non-anhydrous N,N-dimethylformamide (DMF)]. Specific examples of palladium salts which can be advantageously used for the aim are: palladium chloride, palladium bromide, palladium nitrate, palladium acetate, palladium trifluoroacetate, palladium acetylacetonate. Specific examples of ligands which can be advantageously used for the aim are: trialkylphosphines or triarylphosphines, in particular, triphenylphosphine, o-tolylphosphine, m-tolylphosphine, p-tolylphosphine.

The complexes [bis(triphenylphosphine)]-palladium(II) diacetate [Pd(PPh$_3$)$_2$(AcO)$_2$] and dichloro-[bis(triphenylphosphine)]palladium(II) [Pd(PPh$_3$)$_2$Cl$_2$], for example, can be formed in the reaction environment starting from commercial precursors such as triphenylphosphine and palladium (II) acetate or chloride, respectively. For this aim, the two reagents can be mixed, i.e. the disubstituted naphthoheterodiazole compound having general formula (II) and the monostannylated benzodithiophene compound having general formula (III), the palladium salt and the ligand, in the reaction solvent selected from those indicated hereunder [for example, non-anhydrous dimethylsulfoxide (DMSO), non-anhydrous N,N-dimethylformamide (DMF): the reaction mixture obtained is then preferably put under a flow of nitrogen or argon. The mixture is heated to a temperature preferably ranging from 50° C. to 120° C. and the heating is continued until the reaction has been completed, preferably for a time ranging from 15 minutes to 2 hours.

If a preformed palladium complex is used, the two reagents can be mixed, i.e. the disubstituted naphthoheterodiazole compound having general formula (II) and the monostannylated benzodithiophene compound having general formula (III), and the palladium-based catalyst dissolved in the reaction solvent selected from those indicated hereunder [for example, non-anhydrous dimethylsulfoxide (DMSO), non-anhydrous N,N-dimethylformamide (DMF)]: the reaction mixture obtained is then preferably put under a flow of nitrogen or argon. The mixture is heated to a temperature preferably ranging from 50° C. to 120° C. and the heating is continued until the reaction has been completed, preferably for a time ranging from 15 minutes to 2 hours.

In both cases, at the end of the process, the reaction mixture obtained is preferably immersed in ethyl acetate and in a saturated aqueous solution of sodium chloride [NaCl$_{(sat.)}$] if non-anhydrous N,N-dimethylformamide (DMF) has been used, or in dichloromethane and in a saturated aqueous solution of sodium chloride [NaCl$_{(sat.)}$] if non-anhydrous dimethylsulfoxide (DMSO) has been used. Two phases are obtained, which are separated: the desired product is recovered by evaporation from the organic phase, and can be purified by filtration and subsequent crystallization, whereas the aqueous phase is disposed of.

According to a preferred embodiment of the present invention, said disubstituted naphthoheterodiazole compound having general formula (II) and said catalyst containing palladium can be used in molar ratios ranging from 100:0.1 to 100:6, preferably ranging from 100:0.4 to 100:5.

According to a preferred embodiment of the present invention, said disubstituted naphthoheterodiazole compound having general formula (II) can be used at a molar concentration ranging from 0.005 M to 1 M, preferably ranging from 0.01 M to 0.06 M.

According to a preferred embodiment of the present invention, said process can be carried out in the presence of at least one non-anhydrous dipolar aprotic organic solvent.

For the aim of the present description and of the following claims, the term "non-anhydrous dipolar aprotic organic solvent" refers to an aprotic organic solvent containing a quantity of water not lower than or equal to 0.5% (v/v), preferably ranging from 1% (v/v) to 5%/(v/v).

According to a preferred embodiment of the present invention, said non-anhydrous dipolar aprotic organic solvent can be selected, for example, from: non-anhydrous dimethylsulfoxide (DMSO), non-anhydrous N,N-dimethylformamide (DMF), non-anhydrous N,N-dimethylacetamide (DMAc), non-anhydrous N-methylpyrrolidone (NMP), or mixtures thereof. Said dipolar aprotic organic solvent is preferably non-anhydrous dimethylsulfoxide (DMSO), non-anhydrous N,N-dimethylformamide (DMF).

According to a preferred embodiment of the present invention, said process can be carried out at a temperature ranging from 40° C. to 150° C., preferably ranging from 50° C. to 120° C.

According to a preferred embodiment of the present invention, said process can be carried out for a time ranging from 10 minutes to 10 hours, preferably ranging from 15 minutes to 2 hours.

The disubstituted naphthoheterodiazole compound having general formula (II) can be obtained according to processes known in the art, for example, by halogenation of the corresponding naphthoheterodiazole compounds. Further details relating to said processes can be found, for example, in the article of Smith et al., in "*Journal of Heterocyclic Chemistry*" (1968), Vol. 5, pages 295-297, or in the article of Peng et al., in "*Journal of Materials Chemistry*" (2008), Vol. 18, pages 806-818.

The monostannylated benzodithiophene compound having general formula (III) can be prepared according to the following Scheme 2:

Scheme 2

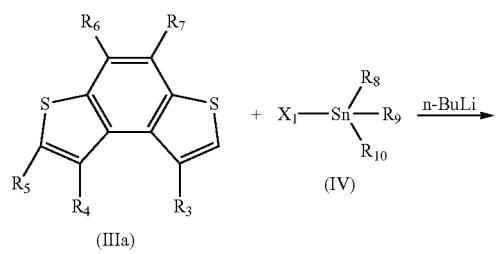

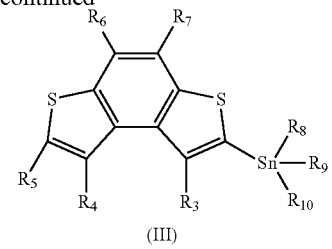

wherein $X_1$ represents a halogen atom selected from chlorine, bromine, iodine, preferably chlorine, $R_3$, $R_4$, $R_5$, $R_6$, $R_7$, $R_8$, $R_9$ and $R_{10}$, have the same meanings described above, by stannylation of a benzodithiophene compound having general formula (IIIa) with a trialkyl- or triaryl-tin halide having general formula (IV). Said stannylation reaction is carried out in the presence of n-butyllithium (n-BuLi) as described, for example, in the article of Bundgaared et al., in "*Macromolecules*" (2006), pages 2823-2831. Further details are provided in the following examples.

The benzodithiophene compound having general formula (IIIa) can be prepared according to processes known in the art. It should be noted, however, that for the aim of the present invention, the benzodithiophene compound having general formula (IIIa) is preferably prepared by means of a process which comprises reacting at least one monohalogenated dithiophene compound having general formula (V):

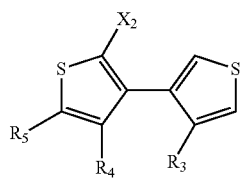

wherein $X_2$ represents a halogen atom selected from iodine, chlorine, bromine, preferably iodine, and $R_3$, $R_4$ and $R_5$ have the same meanings described above, with at least one internal alkine having general formula (VI):

wherein $R_6$ and $R_7$ have the same meanings described above; in the presence of at least one catalyst containing palladium and of at least one co-catalyst containing copper in oxidation state +1 having general formula (VII):

$$CuX_3 \quad (VII)$$

wherein $X_3$ represents a halogen atom selected from iodine, chlorine, bromine, preferably iodine.

Further details relating to the above process can be found in Italian patent application MI2012A002052 in the name of the Applicant, whose content is incorporated herein as reference.

As described above, said disubstituted naphthoheterodiazole compound having general formula (I) can be advantageously used as a spectrum converter in luminescent solar concentrators (LSCs), in their turn capable of enhancing the performances of photovoltaic devices (or solar devices) such as, for example, photovoltaic cells (or solar cells), photovoltaic modules (or solar modules), on both rigid and flexible supports.

Said luminescent solar concentrators (LSCs) can be prepared, for example, by the dispersion in the molten state of said disubstituted naphthoheterodiazole compound having general formula (I) in polymeric materials such as, for example, polymethylmethacrylate (PMMA), polystyrene (PS), polyvinyl acetate (PVA).

Consequently, a further object of the present invention relates to a luminescent solar concentrator (LSC) including at least one disubstituted naphthoheterodiazole compound having general formula (I).

A further object of the present invention relates also to a luminescent solar concentrator (LSC) including at least one compound having formula (Ia).

The luminescent solar concentrators (LSCs) object of the present invention can be produced in the form of prisms or of polymeric sheets to be coupled with photovoltaic devices (or solar devices). Alternatively, according to a different known construction technique, the luminescent solar concentrators (LSCs) can be obtained by depositing a thin film laid on the surface of a sheet or of a transparent prism made of an organic glassy material such as, for example, polymethylmethacrylate (PMMA) or inorganic such as, for example, glass.

A further object of the present invention relates to a photovoltaic device (or solar device) comprising a luminescent solar concentrator (LSC) including at least one disubstituted naphthoheterodiazole compound having general formula (I).

A further object of the present invention also relates to a photovoltaic device (or solar device) comprising a luminescent solar concentrator (LSC) including at least one compound having formula (Ia).

Said photovoltaic device (or solar device) can typically include at least one photovoltaic cell (or solar cell) positioned on the edges of a sheet comprising at least one disubstituted naphthoheterodiazole compound having general formula (I) or at least one compound having formula (Ia).

Some illustrative and non-limiting examples are provided for a better understanding of the present invention and for its practical embodiment.

EXAMPLE 1

Synthesis of tri-n-butyl(7,8-dibutylbenzo[1,2-b:4,3-b']dithien-5-yl)stannane Having Formula (IIIc)

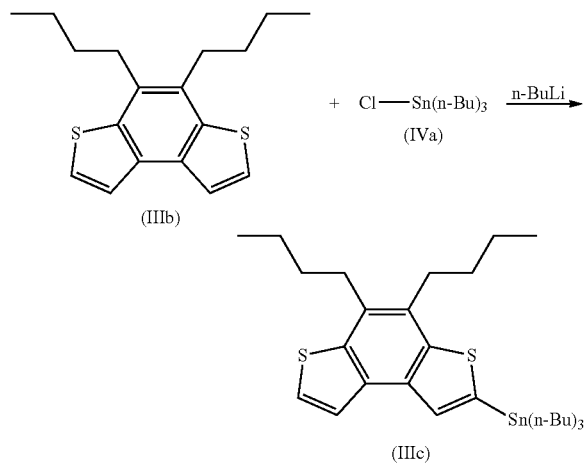

In a 250 ml three-necked glass flask, equipped with magnetic stirring, an isobar drip funnel, two insufflators with taps and a perforable stopper, one insufflator was connected to the argon (Ar) line and the other to the vacuum pump. The insufflator connected to the argon (Ar) line was closed, that connected to the vacuum pump was opened and the vacuum pump was activated: the glass flask was contemporaneously heated to a temperature of 150° C., for 5 minutes, with a hot air gun, to desorb the humidity.

Said glass flask was cooled to room temperature (25° C.) and subjected to the so-called vacuum/argon (Ar) technique, i.e. the insufflator connected to the argon line (Ar) was opened for 30 seconds and a vacuum was then re-applied: said vacuum/argon (Ar) technique was repeated five times. 5.31 g (17.6 mmoles) of 7,8-di-n-butylbenzo[1,2-b:4,3-b'] dithiophene having formula (IIIb) (obtained as described in Example 1 of Italian patent application MI2012A002052) and 125 ml of freshly distilled tetrahydrofuran (THF) (Carlo Erba), were subsequently charged under a flow of argon (Ar). The whole mixture was subjected to magnetic stirring and the glass flask was immersed in a cooling bath containing dry ice/acetone, at −78° C. 12 ml (19.2 mmoles) of n-butyllithium (n-BuLi) 1.6 M in n-hexane (Aldrich) were then introduced, in 30 minutes, by means of a drip funnel: the whole was left, under vigorous stirring, at −78° C. for a further 30 minutes.

The cooling bath containing dry ice/acetone was subsequently substituted with a cooling bath containing water/ice and the temperature was brought to 0° C.: the whole was left at 0° C., for 90 minutes. At the end, the glass flask was re-positioned in the cooling bath containing dry ice/acetone, at −78° C., and 5.8 ml (7.0 g, 21 mmoles) of tri-n-butyltin chloride having formula (IVa) (Aldrich) were introduced by means of another drip funnel previously anhydrified, over a period of 20 minutes. The cooling bath containing dry ice/acetone was then removed and the whole was left at room temperature (25° C.), for 19 hours. The advance degree of the reaction was then controlled, operating as follows: 0.1 ml of reaction mixture were removed from the glass flask and introduced into a test-tube containing 2 ml of ethyl ether (Aldrich) and 3 ml of a saturated aqueous solution of sodium bicarbonate [NaHCO$_{3(sat.)}$] (prepared with sodium bicarbonate of Aldrich) and the whole was subjected to stirring, obtaining a biphasic system comprising a prevalently ether phase and a prevalently aqueous phase. The prevalently ether phase was separated and subjected to thin layer chromatography (TLC) on silica gel using n-heptane (Carlo Erba) as eluent and an ultraviolet (UV) lamp as detector at 256 nm: said analysis indicated that tri-n-butyl(7,8-dibutylbenzo[1,2-b:4,3-b'] dithien-5-yl)stannane having formula (IIIc) had been formed with a yield equal to 100%.

The reaction mixture was then immersed in a separator funnel containing ethyl ether (Aldrich) and a saturated aqueous solution of sodium bicarbonate [NaHCO$_{3(sat.)}$] (prepared with sodium bicarbonate of Aldrich): the whole mixture was subjected to stirring obtaining a biphasic system comprising a prevalently ether phase and a prevalently aqueous phase. The prevalently ether phase was separated and extracted three times with a saturated aqueous solution of sodium bicarbonate [NaHCO$_{3(sat.)}$] (prepared with sodium bicarbonate of Aldrich) to remove the tetrahydrofuran (THF) and the lithium chloride (LiCl) formed by the reaction: the aqueous phases obtained were joined and extracted twice with ethyl ether (Aldrich). The organic phases obtained at the end of the extractions were joined, dried on anhydrous sodium sulfate [Na$_2$SO$_{4(anhydrous)}$] (Aldrich) for 45 minutes and subsequently filtered on cotton. The filtered solution was subjected to evaporation by means of a rotating evaporator obtaining 11.7 g of an oil containing: tri-n-butyltin chloride having formula (IVa) in excess and 10.4 g of tri-n-butyl(7,8-dibutyl-benzo[1,2-b:4,3-b']dithien-5-yl)stannane having formula (IIIc) (100% yield).

EXAMPLE 2

Synthesis of 4,9-bis(7',8'-dibutylbenzo[1',2'-b':4',3'-b"]dithien-5'-yl)naphtho[2,3-c]-[1,2,5]thiadiazole Having Formula (Ia)

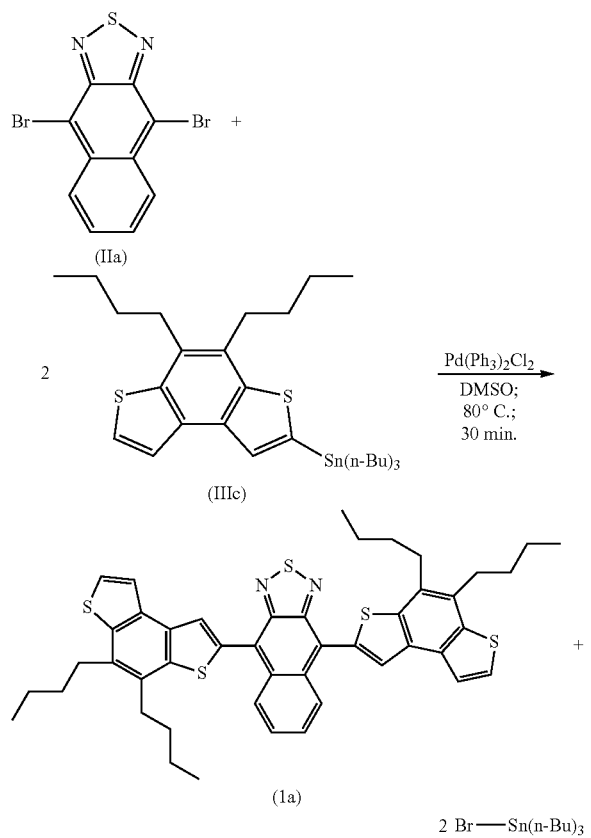

10.7 g (17.6 mmoles) of tri-n-butyl(7,8-dibutylbenzo[1,2-b:4,3-b']dithien-5-yl)-stannane having formula (IIIc) obtained in Example 1, 2,89 g (8.4 mmoles) of 4,9-dibromonaphtho-[2,3-c][1,2,5]thiadiazole having formula (IIa) (Santai Labs), 800 ml of non-anhydrous dimethylsulfoxide (DMSO) (Acros Organics) and 295 mg (0.42 mmoles) of dichloro[bis-(triphenylphosphine)]palladium(II) [Pd(PPh$_3$)$_2$Cl$_2$] (Aldrich), were charged into a 1 liter three-necked glass flask, equipped with magnetic stirring, an insufflator with a tap, a thermometer with a ground-glass cone and stopper: the whole was subjected to stirring and put under a flow of argon (Ar).

The glass flask was then immersed in a preheated bath to bring the temperature of the reaction mixture to about 80° C. and left at this temperature for 30 minutes. The advance degree of the reaction was then controlled, operating as follows: 0.1 ml of reaction mixture were removed from the glass flask and introduced into a test-tube containing 2 ml of dichloromethane (CH$_2$Cl$_2$) (Aldrich) and 3 ml of a saturated aqueous solution of sodium chloride [NaCl$_{(sat.)}$] (prepared with sodium chloride of Aldrich) and the whole was subjected to stirring, obtaining a biphasic system comprising a prevalently organic phase and a prevalently aqueous phase. The prevalently organic phase was separated and subjected to thin layer chromatography (TLC) on silica gel using a mixture of n-heptane (Carlo Erba)/dichloromethane (CH$_2$Cl$_2$) (Aldrich) (1/1, v/v) as eluent and an ultraviolet (UV) lamp as detector at 365 nm: said analysis indicated that 4,9-bis(7',8'-dibutylbenzo[1',2'-b':4',3'-b"]dithien-5'-yl)naphtho-[2,3-c]-[1,2,5]thiadiazole having formula (Ia) had been formed with a yield equal to 95%.

The reaction mixture was then immersed in a separator funnel containing dichloromethane (CH$_2$Cl$_2$) (Aldrich) and a saturated aqueous solution of sodium chloride [NaCl$_{(sat.)}$] (prepared with sodium chloride of Aldrich): the whole was subjected to stirring obtaining a biphasic system comprising a prevalently organic phase and a prevalently aqueous phase. The prevalently organic phase was separated and extracted three times with a saturated aqueous solution of sodium chloride [NaCl$_{(sat.)}$] (prepared with sodium chloride of Aldrich) to remove the dimethylsulfoxide (DMSO): the aqueous phases obtained were joined and extracted twice with dichloromethane (CH$_2$Cl$_2$) (Aldrich). The organic phases obtained at the end of the extractions were joined, dried on anhydrous calcium chloride [CaCl$_{2(anhydrous)}$] (Aldrich) for 45 minutes and filtered on a Buchner funnel, under vacuum. The solution obtained after filtration was subjected to evaporation by means of a rotating evaporator and the resulting oil was treated with an oil pump to eliminate the traces of solvent still present, obtaining a residue which was dissolved in the minimum possible volume of dichloromethane (CH$_2$Cl$_2$), 10 g of silica (SiO$_2$) (Carlo Erba) were subsequently added and the mixture was then dried again with a rotating evaporator.

The powder obtained was placed on top of a silica panel (SiO$_2$) (Carlo Erba) to allow it to be filtered, initially with n-heptane (Aldrich), to remove all the impurities having a lower polarity, and subsequently with a mixture of n-heptane (Carlo Erba)/dichloromethane (CH$_2$Cl$_2$) (Aldrich) (1/1, v/v) to elute the 4,9-bis(7',8'-dibutylbenzo[1',2'-b':4',3'-b"]dithien-5'-yl)naphtho-[2,3-c]-[1,2,5]thiadiazole having formula (Ia), operating in a gradient of eluent with an increasing polarity until pure dichloromethane (CH$_2$Cl$_2$) (Aldrich) to complete the filtration. The filtrate obtained was evaporated to dryness by means of a rotating evaporator, obtaining a solid which was dissolved in the minimum possible volume of dichloromethane (CH$_2$Cl$_2$) (Aldrich) and brought to boiling point, under a flow of nitrogen (N$_2$), the volume was then doubled with t-butylmethylether (Aldrich), brought again to boiling point and left to boil until the volume was halved. The whole was left to cool to room temperature (25° C.) and was then cooled to 0° C. with a water and ice bath, subjected to filtration and washed with t-butylmethylether (Aldrich) at 0° C., obtaining 6.28 g of dark brick-red crystals of pure 4,9-bis(7',8'-dibutylbenzo[1',2'-b':4',3'-b"]dithien-5'-yl)naphtho-[2,3-c]-[1,2,5]thiadiazole having formula (Ia) (yield 95%).

EXAMPLE 3

6 g of polymethylmethacrylate Altuglas VSUVT 100 (PMMA) and 183.8 mg of 4,9-bis(7',8'-dibutylbenzo[1',2'-b':4',3'-b"]dithien-5'-yl)naphtho-[2,3-c]-[1,2,5]thiadiazole having formula (Ia) (F521) obtained as described in Example 2, were dissolved in 30 ml of 1,2-dichlorobenzene (Aldrich). The solution obtained was subsequently uniformly deposited on a sheet of polymethylmethacrylate Altuglas VSUVT 100 (PMMA) (dimensions 300 mm×90 mm×6 mm) with the use of a filmograph of the Doctor Blade type and the solvent was left to evaporate at room temperature (25° C.), under a light stream of air, for 24 hours. A transparent sheet (sheet 1) was obtained, having a purple colour conferred to it by the film whose thickness proved to range from 50 μm to 100 μm.

A photovoltaic cell IXYS-KXOB22-12 having a surface of 1.2 cm², was then applied to one of the edges of the polymeric sheet.

The main side of the polymeric sheet [that coated with the thin film containing 4,9-bis(7',8'-dibutylbenzo[1',2'-b':4',3'-b"]dithien-5'-yl)naphtho-[2,3-c]-[1,2,5]thiadiazole having formula (Ia) (F521)] was then illuminated with a light source having a power of 1 sun (1000 W/m²), and the electric power generated by the illumination was measured.

The power measurements (P) were carried out by illuminating a portion of the sheet having dimensions equal to 100 mm×90 mm, at an increasing distance (d) from the edge on which the photovoltaic cell was fixed. These measurements at a variable distance from the photovoltaic cell allow the contribution of optional waveguide, edge and self-absorption effects to be quantified.

FIG. 1 shows the curve relating to the generated power value (P) expressed in mW (reported in the ordinate), in relation to the distance (d) from the edge on which the photovoltaic cell was fixed, expressed in cm (reported in the abscissa).

It can be seen how, in the absence of edge effects, the average power generated is equal to 10.08 mW (FIG. 1).

EXAMPLE 4

Comparative 6 g of polymethylmethacrylate Altuglas VSUVT 100 (PMMA) and 49.5 mg of 4,7-di(thien-2'-yl)-2,1,3-benzothiadiazole (DTB), were dissolved in 30 ml of 1,2-dichlorobenzene (Aldrich). The solution obtained was subsequently uniformly deposited on a sheet of polymethylmethacrylate Altuglas VSUVT 100 (PMMA) (dimensions 300 mm×90 mm×6 mm) with the use of a filmograph of the Doctor Blade type and the solvent was left to evaporate at room temperature (25° C.), under a light stream of air, for 24 hours. A transparent sheet (sheet 2) was obtained, having a yellow colour conferred to it by the film whose thickness proved to range from 50 μm to 100 μm.

A photovoltaic cell IXYS-KXOB22-12 having a surface of 1.2 cm², was then applied to one of the edges of the polymeric sheet.

The power measurements (P) were carried out by illuminating a portion of the sheet having dimensions equal to 100 mm×90 mm, at an increasing distance (d) from the edge on which the photovoltaic cell was fixed. These measurements at a variable distance from the photovoltaic cell allow the contribution of optional waveguide, edge and self-absorption effects, to be quantified.

FIG. 1 shows the curve relating to the generated power value (P) expressed in mW (reported in the ordinate), in relation to the distance (d) from the edge on which the photovoltaic cell was fixed, expressed in cm (reported in the abscissa).

It can be seen how, in the absence of edge effects, the average power generated is equal to 5.01 mW (FIG. 1) therefore lower than that generated using 4,9-bis(7',8'-dibutyl-benzo[1',2'-b':4',3'-b"]dithien-5'-yl)naphtho-[2,3-c]-[1,2,5] thiadiazole having formula (Ia) (F521)] (Example 3) according to the present invention.

The invention claimed is:
1. A process for preparing a disubstituted naphthoheterodiazole compound having a formula (I):

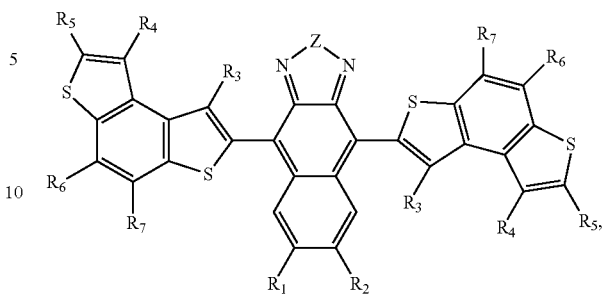

the process comprising reacting at least one disubstituted naphthoheterodiazole compound having a formula (II):

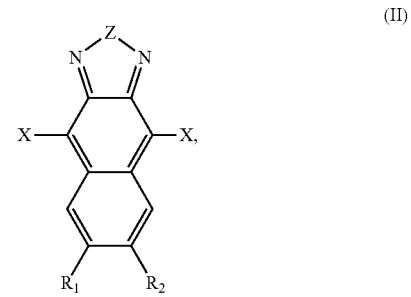

wherein:
X represents a halogen atom selected from the group consisting of chlorine, bromine, and iodine;
Z represents a heteroatom selected from the group consisting of oxygen, sulfur, selenium, and tellurium; and
$R_1$ and $R_2$ are each independently a hydrogen atom, n-butyl, iso-butyl, sec-butyl, or t-butyl,
with at least one monostannylated benzodithiophene compound having a formula (III):

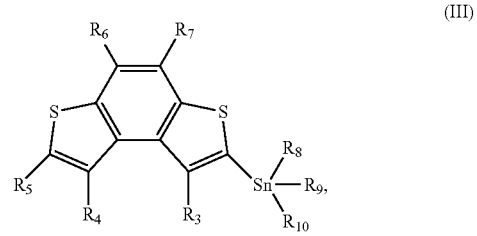

in the presence of at least one non-anhydrous dipolar aprotic organic solvent and at least one catalyst comprising palladium,
wherein:
$R_3$, $R_4$, $R_5$, $R_6$ and $R_7$ each independently represents a hydrogen atom, n-butyl, iso-butyl, sec-butyl, or t-butyl; and
$R_8$, $R_9$ and $R_{10}$ each independently represents a hydrogen atom, an optionally substituted linear or branched $C_1$-$C_{20}$ alkyl group, or an optionally substituted cycloalkyl group.
2. The process according to claim 1, wherein the disubstituted naphthoheterodiazole compound having the formula (II) and the monostannylated benzodithiophene compound having the formula (III) are reacted in a molar ratio ranging from 1:2 to 1:4.

3. The process according to claim 1, wherein the disubstituted naphthoheterodiazole prepared is 4,9-bis(7',8'-dibutyl-benzo[1',2'-b':4',3'-b"]dithien-5'-yl)-naphtho[2,3-c][1,2,5]thiadiazole having a formula (Ia)

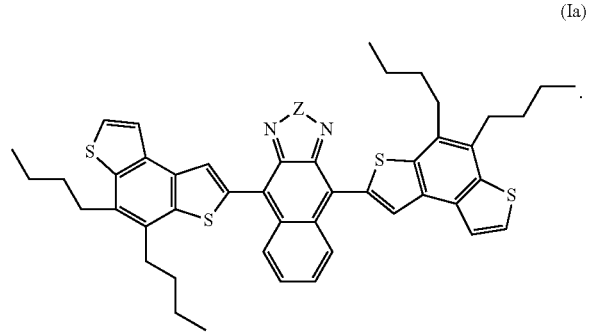

(Ia)

4. The process according to claim 1, wherein the catalyst comprises palladium in an oxidation state of (0) or (II).

5. The process according to claim 1, wherein the catalyst is dichloro-[bis(triphenylphosphine)]palladium(II) [Pd(PPh$_3$)$_2$Cl$_2$].

6. The process according to claim 1, wherein the disubstituted naphthoheterodiazole compound having the formula (II) and the catalyst are present in a molar ratio ranging from 100:0.1 to 100:6.

7. The process according to claim 1, wherein the disubstituted naphthoheterodiazole compound having the formula (II) is present in a molar concentration ranging from 0.005 M to 1 M.

8. The process according to claim 1, wherein the non-anhydrous dipolar aprotic organic solvent is at least one member selected from the group consisting of non-anhydrous dimethylsulfoxide (DMSO), non-anhydrous N,N-dimethylformamide (DMF), non-anhydrous N,N-dimethylacetamide (DMAc), and non-anhydrous N-methylpyrrolidone (NMP).

9. The process according to claim 1, wherein the reacting occurs at a temperature ranging from 40° C. to 150° C.

10. The process according to claim 1, wherein the reacting occurs for a time ranging from 10 minutes to 10 hours.

\* \* \* \* \*